United States Patent
Koop

(10) Patent No.: US 10,024,786 B2
(45) Date of Patent: Jul. 17, 2018

(54) METHOD FOR CALIBRATING AN OPTICAL FLUID SENSOR

(71) Applicant: Robert Bosch GmbH, Stuttgart (DE)

(72) Inventor: Paul Koop, Stuttgart (DE)

(73) Assignee: ROBERT BOSCH GMBH, Stuttgart (DE)

(*) Notice: Subject to any disclaimer, the term of this patent is extended or adjusted under 35 U.S.C. 154(b) by 0 days.

(21) Appl. No.: 15/345,987

(22) Filed: Nov. 8, 2016

(65) Prior Publication Data

US 2017/0138843 A1    May 18, 2017

(30) Foreign Application Priority Data

Nov. 18, 2015  (DE) .................... 10 2015 222 769

(51) Int. Cl.
G01N 21/27    (2006.01)
G01N 21/552   (2014.01)

(52) U.S. Cl.
CPC ......... *G01N 21/278* (2013.01); *G01N 21/552* (2013.01)

(58) Field of Classification Search
CPC .................................................. G01N 21/278
USPC ........................................................ 356/243.1
See application file for complete search history.

(56) References Cited

U.S. PATENT DOCUMENTS

| | | | | |
|---|---|---|---|---|
| 4,306,152 A * | 12/1981 | Ross | ................... | G01N 21/3577 250/343 |
| 4,481,419 A * | 11/1984 | Persyk | ................... | G01T 1/295 250/363.06 |
| 4,989,991 A * | 2/1991 | Pecot | ................... | G01J 5/0003 324/750.03 |
| 5,416,575 A * | 5/1995 | Schwartz | ............. | G01N 21/278 356/243.1 |
| 2003/0223082 A1 * | 12/2003 | Trantow | ................ | G01B 5/205 356/601 |
| 2004/0156757 A1 * | 8/2004 | Lustig | .................. | B01J 19/0046 422/130 |
| 2006/0053862 A1 * | 3/2006 | Mayer | ................ | G01N 33/0006 73/1.06 |
| 2006/0138392 A1 * | 6/2006 | Bowden | ................ | B82Y 30/00 257/1 |

* cited by examiner

*Primary Examiner* — Tarifur Chowdhury
*Assistant Examiner* — Omar Nixon
(74) *Attorney, Agent, or Firm* — Norton Rose Fulbright US LLP; Gerard Messina

(57) ABSTRACT

A method for calibrating an optical fluid sensor, the method including providing a calibration element having defined properties similar to those of a fluid to be measured; simulating optical characteristics of the fluid to be measured, with the aid of the calibration element, a measuring radiation being routed onto the calibration element, and evaluating the measuring radiation modified by the calibration element, at least one calibration point of the fluid being ascertained with the aid of the calibration element.

15 Claims, 4 Drawing Sheets

METHOD FOR CALIBRATING AN OPTICAL FLUID SENSOR

CROSS REFERENCE

The present application claims the benefit under 35 U.S.C. § 119 of German Patent Application No. DE 102015222769.3 filed on Nov. 18, 2015, which is expressly incorporated herein by reference in its entirety.

FIELD

The present invention relates to a method for calibrating an optical fluid sensor. The present invention furthermore relates to a calibration element for an optical fluid sensor. In addition, the present invention pertains to a calibration device for an optical fluid sensor.

BACKGROUND INFORMATION

Conventional optical measuring systems are used for detecting certain components in fluids or gases. Individual substances in said media or a substance concentration of these media can be ascertained with the aid of a spectroscopic measurement, such measurements requiring at least one optical detector and at least one optical radiation source. Since these components are usually not resistant to all fluid media to be tested, they must be protected.

Generally, the optical fluid sensors are calibrated following the final production step in order to achieve the required accuracy despite the tolerances of the individual components and the optical path. To do so, for example, the medium or fluid to be measured is introduced in a certain concentration, and a correction value or a correction function is calculated subsequently. Depending on the sensor type, this requires one or several calibration point(s). This constitutes a disadvantage in mass production, especially in the case of fluid sensors, since it is labor- and cost-intensive, and possibly even dangerous if flammable fluids are involved.

Optical fluid measuring systems may be configured for the following measuring principles:

Absorption-measurement methods, in which the fluid to be measured is situated between the radiation source and the detector, a distance between the radiation source and the detector being a function of the application requirements;

Reflection measurement methods, in which the fluid is characterized on the basis of reflection characteristics;

ATR measurement methods (attenuated total reflection) represent a measuring technology of infrared spectroscopy for checking the surface of opaque substances, such as lacquer layers or polymer foils, and also fluid samples such as solvent mixtures. An intensity of reflected light is measured in the process, thereby allowing conclusions with regard to the absorbing fluid.

All enumerated measuring principles require a calibration of the fluid sensors independently of the application.

SUMMARY

Therefore, it is an object of the present invention to provide an improved and cost-efficient method for calibrating an optical media sensor.

According to a first aspect, the objective is achieved by a method for calibrating an optical fluid sensor, the method having the steps:

Providing a calibration element having defined properties similar to those of a fluid to be measured;

Simulating optical properties of the fluid to be measured with the aid of the calibration element, a measurement radiation being routed onto the calibration element; and Evaluating the measurement radiation modified by the calibration element, at least one calibration point of the fluid being produced in the process with the aid of the calibration element.

In this way, a rapid and cost-effective calibration without the use of the measuring fluid is advantageously able to be carried out. This is achieved with the aid of a simulation process, in which a calibration element is only temporarily provided in a fluid measuring channel. Overall, this contributes to an efficient production of optical sensors for media detection.

According to a second aspect, the objective is achieved by a calibration element for optical fluid sensors, which is characterized by the fact that optical properties of a fluid are able to be simulated by the calibration element during a calibration process, at least one calibration point for the fluid sensor being able to be recorded.

In this manner, a generally conventional optical fluid sensor having a calibration element is able to perform a calibration process of the fluid to be measured in the absence of the actual measuring fluid.

Preferred specific embodiments of the method are described herein.

In one advantageous further refinement of the method, the optical properties of the fluid are simulated by a defined thickness of the calibration element. This allows a simple adjustment of optical properties.

In another advantageous further refinement of the method, a coating of the calibration element simulates the optical properties of the fluid. This provides an alternative, easily realizable method for simulating optical properties of the fluid.

Another advantageous further refinement of the method is characterized by a simulation of the optical properties of the fluid through effects at a boundary surface of the calibration element. This provides another possibility for simulating optical properties of the fluid, via reflections at boundary surfaces of what is known as an ATR crystal.

A characteristic of another advantageous further refinement of the calibration element is that the calibration element can be introduced into a fluid channel during the calibration process and be removed again from the fluid channel following the calibration process. This provides a simple method that also lends itself to an automated execution. Overall, this contributes to a rapid and cost-effective calibration of the fluid sensor.

In another advantageous further development of the calibration element, a reflection behavior of the fluid is able to be simulated with the aid of a reflection layer applied on the calibration element. This makes it possible to simulate optical properties of the fluid with the aid of the reflection principle.

Another advantageous further refinement of the calibration element is characterized by the fact that it allows a simulation of a transmittance behavior of the fluid via a thickness of the calibration element. This makes it possible to simulate a calibration process according to the transmittance measuring principle.

Another advantageous further refinement of the calibration element is characterized by the fact that the calibration element may be placed on boundary surfaces of an ATR crystal. This enables an uncomplicated calibration of a fluid sensor which is based on the ATR measuring principle.

Another advantageous further refinement of the calibration element is characterized by the fact that the calibration element is a vessel that has a defined length, in which a fluid having a defined concentration is situated. This makes it possible to simulate a fluid via the parameters of length and concentration.

In one advantageous further refinement of the calibration element, the calibration element is a Si wafer. This provides a solid element by which optical properties may be simulated in an uncomplicated manner.

Another advantageous further refinement of the calibration element is characterized by the fact that the calibration element is a gel. This provides a further alternative calibration element that has advantageous application characteristics.

In the following text, the present invention will be described in detail with further features and advantages on the basis of multiple figures. All of the disclosed features form the subject matter of the present invention, regardless of their presentation in the specification and in the figures. Identical or functionally equivalent elements have been provided with the same reference numerals. The figures are specifically intended to illustrate the principles of the present invention, and are not necessarily shown true to scale.

Disclosed method features analogously result from correspondingly disclosed device features, and vice versa. This means, in particular, that features, technical advantages and specific embodiments pertaining to the method for calibrating an optical fluid sensor result in an analogous manner from corresponding developments, features and advantages pertaining to the calibration element, and vice versa.

BRIEF DESCRIPTION OF EXAMPLE EMBODIMENTS

Figure 1:
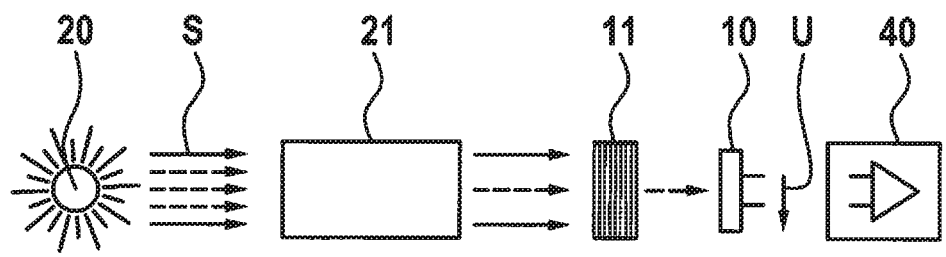
FIG. 1 shows a conventional topology of an optical fluid sensor.

FIG. 1 shows an array of a conventional spectroscopic sensor device in greatly simplified form. A radiation source 20 emits a measuring or test radiation S, which passes through a test medium, or test fluid 21, in the form of a gas or a fluid that represents an absorption path for measuring radiation S. Situated downstream from the absorption path is an optical filter 11, which filters out a wavelength region of measuring radiation S and forwards the filtered-out region to a detector device 10, which generates an electric voltage U therefrom. Electric voltage U is evaluated with the aid of an electronic evaluation circuit 40, thereby making it possible to ascertain specific properties of, or changes in, test medium 21.

In accordance with the present invention, a calibration method for an optical fluid sensor is provided, preferably for use in production, which eliminates a need for the presence of the fluid in the measuring space or directly at the optical measuring element or routing element.

In an advantageous manner, the provided method makes it possible to adjust or calibrate an optical fluid sensor without using the actual measuring fluid in the process. The calibration is possible in that the corresponding absorption in the optical path is simulated with the aid an additional material (such as a solid or a vessel including a fluid with a higher concentration). This element, which features corresponding transmittance characteristics that are adapted to the individual application, is positioned in the optical path (ideally, directly upstream from the detector) in such a way that a calibration point is recordable, which must correlate with a specific concentration of the measuring fluid. On this basis, a required correction function may be calculated and stored in the fluid sensor.

This calibration is able to simplify the entire calibration process considerably. The production lines do not have to be configured for the particular fluid, such as diesel, ethanol, etc. In addition, the calibration process is accelerated significantly since waiting times (required for gas sensors, in particular) until the measuring fluid for the calibration has been homogeneously distributed in the measuring space are eliminated.

Another advantage, especially in the case of fluid sensors, is an avoidance of contamination of the fluid sensor by the fluid prior to the installation. Undesired drying-out of measuring fluid residue during transportation will not occur because there is no contact between the fluid sensor and the fluid until the fluid sensor is installed.

Figure 2:
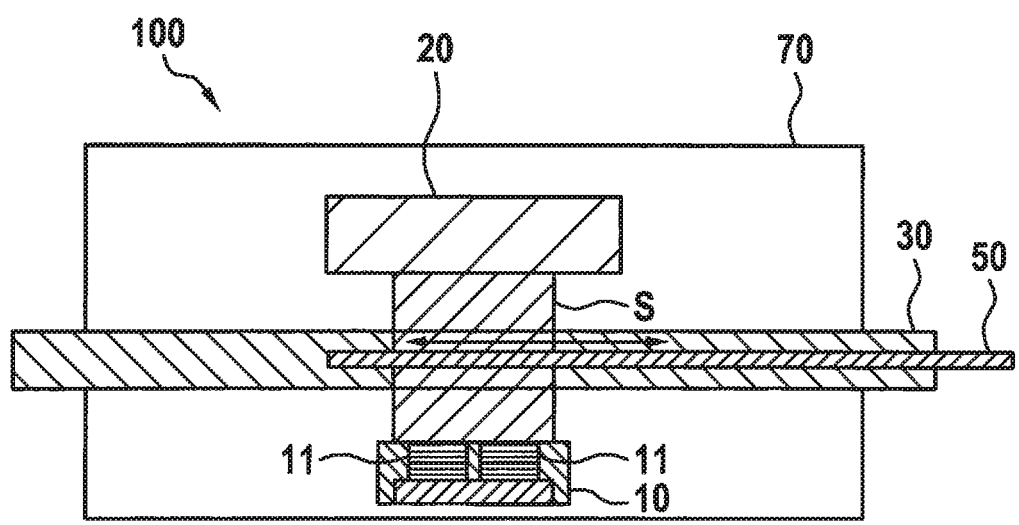
FIG. 2 shows a basic representation of a specific embodiment of a method for calibrating an optical fluid sensor.

FIG. 2 shows a cross-sectional view of one possible variant of an optical fluid sensor 100 situated in a housing 70, by which the proposed method is executed. In a functional, normal operation of fluid sensor 100, in the case of a fluid sensor, a fluid 21 to be measured or a fluid medium or measuring fluid (not shown), in which specific components in the fluid are to be detected (such as a bio diesel concentration in diesel), is routed through a fluid channel 30 (e.g., in the form of a pipe), which is is resistant to fluid 21 and also provides transparency for a relevant wavelength region that is sufficient for the measurement.

A radiation source 20 (typically a broadband source, e.g., an infrared source) having a suitable wavelength region is placed on one side of fluid channel 30, and an optical detector device 10 is placed on the other side of fluid channel 30. A measuring beam S, generated by radiation source 20, is guided through fluid channel 30 including fluid 21. A portion of measuring radiation S is absorbed by fluid 21. The arriving radiant flux is filtered by an optical filter 11, which has a two-channel design (measuring channel and reference channel) in the configuration of FIG. 2, and is detected by detector device 10. In this way, it is prevented that radiation source 20, detector device 10 and other sensor components come into contact with fluid 21.

To calibrate this configuration without using actual fluid 21 with different concentrations of the components to be measured therein, a calibration element 50 made of a solid (e.g., in the form of a Si wafer) is positioned in such a way that the absorption caused by calibration element 50 corresponds to a known and previously already ascertained configuration of the measuring fluid. In other words, this means that calibration element 50 has defined optical properties that are similar to those of fluid 21 to be measured. Optionally, calibration element 50 may additionally be coated in order to provide the required optical properties.

As shown in FIG. 2, calibration element 50 is placed directly in the optical path in fluid channel 30, and a first measuring point is recorded in the process. When calibration element 50 is then removed again from fluid channel 30, the zero point may be recorded in addition, which corresponds to a fluid concentration of zero ("two-step calibration"). This makes it possible to calculate a correction function and to store it in fluid sensor 100. Some applications may require further calibration points. Toward this end, another wafer having different transmittance properties, which correspond to other concentrations of the measuring fluid in each case, may be positioned in the measuring path of fluid channel 30. Also conceivable is that calibration element 50 has different coatings, and different measuring points are able to be recorded using an insertion distance into fluid channel 30 that is selected according to the particular coating.

As an alternative, it is also possible to place a suitably shaped vessel including measuring fluid, preferably with a higher concentration, in the optical measuring path (not shown). Said vessel must provide a wavelength that is relevant for the application with transparent material. Exact technical parameters of this vessel including its content may be ascertained ahead of time with the aid of a reference device.

One further realization possibility consists of introducing the absorption material or the vessel used for the calibration into the measuring path already during production. This may simultaneously be used as contamination protection or as spacer. A calibration point may be recorded directly following the final production step. The material is then removed from the optical path, for instance in order to carry out a zero point measurement.

A gel is also possible as alternative material for calibration element 50.

Figure 3:
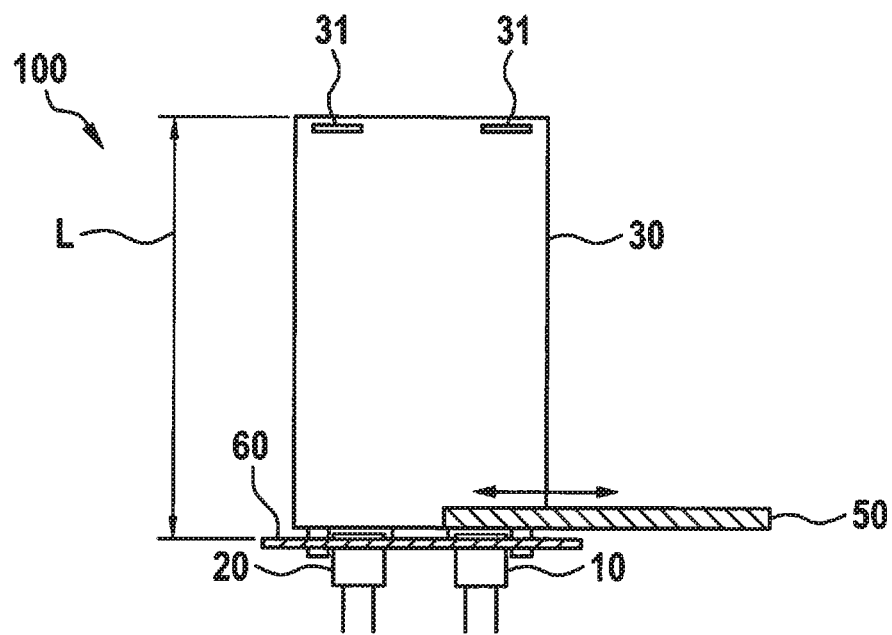
FIG. 3 shows a basic representation of a further specific embodiment of a method for calibrating an optical fluid sensor.

For gas sensors, the calibration may be carried out in the afore-described manner as well, as outlined in principle in FIG. 3. Calibration element 50 or the calibration foil can be applied directly onto the measuring channel of detector device 10 or be positioned there. Toward this end, special fluid supply openings 31 may be provided in fluid channel 30, the fluid channel representing a reflector in its method of functioning. In this way, a corresponding gas concentration in the measuring path is able to be simulated. Depending on the individual requirements, the calibration process may be carried out using a plurality of different materials if this is required by the calibration procedure. A measuring distance L, which represents a reflection length, is suitably selected in each instance.

In the case of a gas sensor, it is furthermore possible to introduce a vessel containing an appropriate gas, which is compressed and pressurized. This makes it possible to simulate the concentration required for the calibration in the entire measuring volume.

Variations of the afore-described alternatives are conceivable as well.

Figure 4:
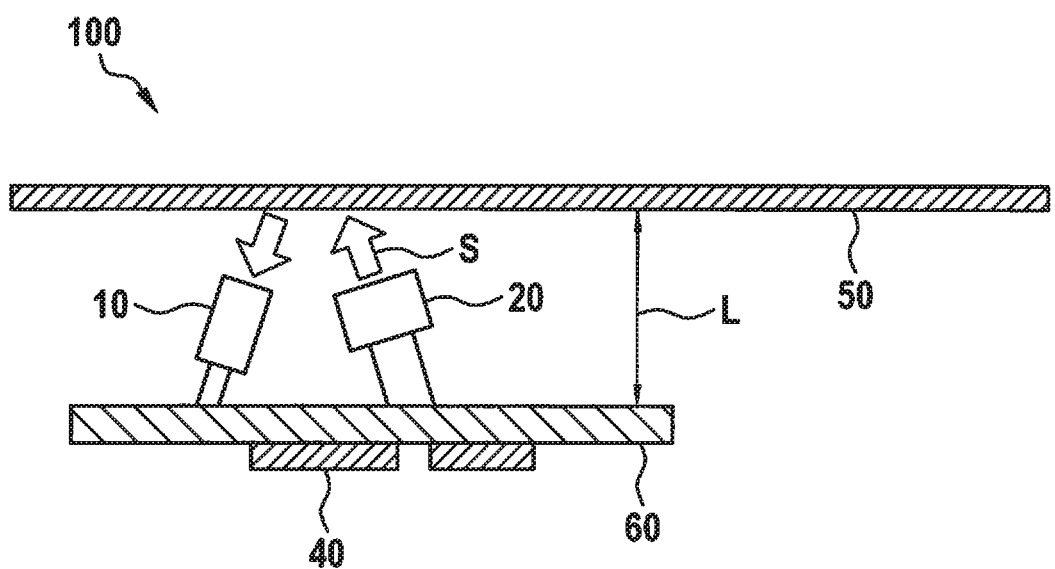
FIG. 4 shows a basic representation of a further specific embodiment of a method for calibrating an optical fluid sensor.

In a reflection- or ATR measuring method, the measuring fluid is positioned in such a way that the application conditions are provided. In the case of an optical fluid sensor 100 operating on the basis of the reflection principle, for example, a suitable calibration element 50 is placed in such a way that the fluid properties for a certain fluid state are simulated (e.g., with regard to concentration, moisture, etc.), as outlined in general in FIG. 4. Calibration element 50 may be developed in the form of a silicon wafer having a suitable reflective coating, which reflects measuring radiation S, generated by radiation source 20, at a suitable measuring distance L and routes it onto detector device 10. It is outlined in FIG. 4 that an electronic evaluation circuit 40 for evaluating reflected measuring radiation S is situated on a circuit board 60. Alternatively, it is also possible to position evaluation circuit 40 externally from optical fluid sensor 100.

Figure 5:
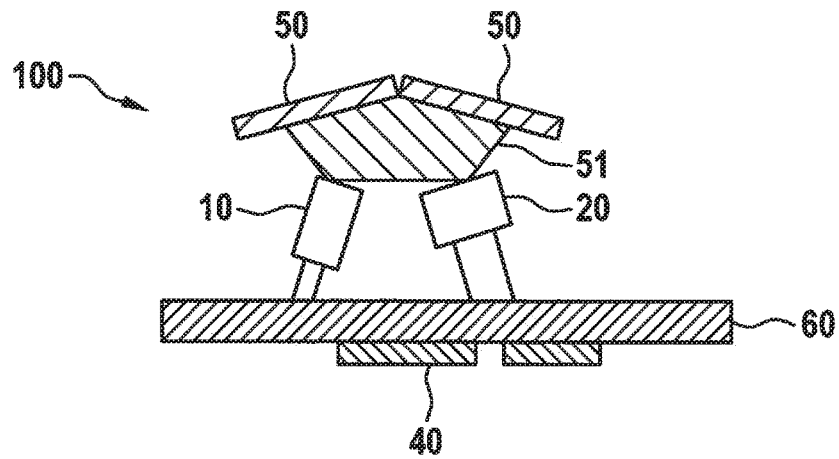
FIG. 5 shows a basic representation of a further specific embodiment of a method for calibrating an optical fluid sensor.

As basically illustrated in FIG. 5, in the ATR measuring method it is possible, for instance, to bring calibration element 50 into temporary contact with an ATR crystal 51 in order to thereby simulate the properties of fluid 21 in the application. This makes it possible to simulate and calibrate different calibration points. Fluid channel 30 with fluid 21 is not shown in FIG. 5 for reasons of clarity. Once the calibration of fluid sensor 100 has taken place, calibration element 50 is removed and ATR crystal 51 is fixed in place on a transparent section of fluid channel 30 for the functional, normal operation of fluid sensor 100.

A number of measuring channels depends on the application; possible, for example, are up to sixteen or possibly even more measuring channels. A detector array having a suitable number of individual detectors or pixels may be used for detector device 10.

Figure 6:
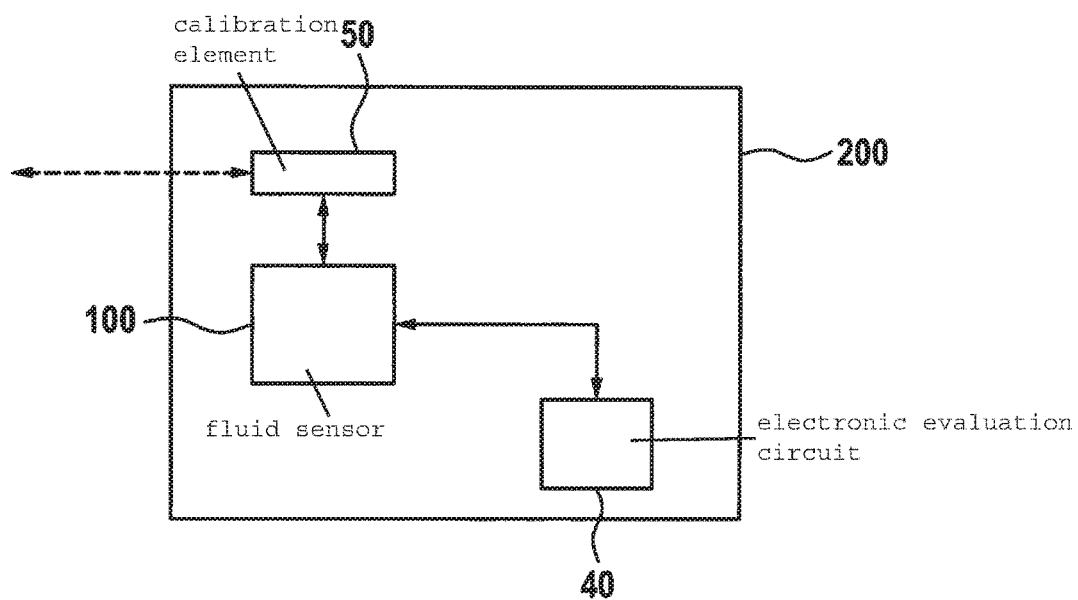
FIG. 6 shows a basic representation of a calibration device for calibrating an optical fluid sensor.

FIG. 6 illustrates a calibration device 200 for an optical fluid sensor 100 in a considerably simplified form. Calibration device 200 is characterized by the fact that afore-described calibration element 50 is functionally connected to fluid sensor 100 during the calibration process, i.e., only temporarily. Once the calibration process has been concluded, calibration element 50 is removed again and fluid sensor 100 can be used for a functional, normal operation. The introduction and the removal of calibration element 50 are indicated by a dashed double arrow.

In an advantageous manner, the method for calibrating gas sensors, fluid sensors (e.g., diesel sensors) or surface sensors may also be used in automation-supported variants. Additional options for realizing the method (not shown in the figures) result from a combination of the afore-described specific embodiments.

The example calibration in accordance with the present invention may advantageously be used for a multitude of optical fluid sensors that operate in the near-infrared range, in the visible or in other optical ranges. The type of detector and radiation source must be mutually adapted in each case.

Figure 7:
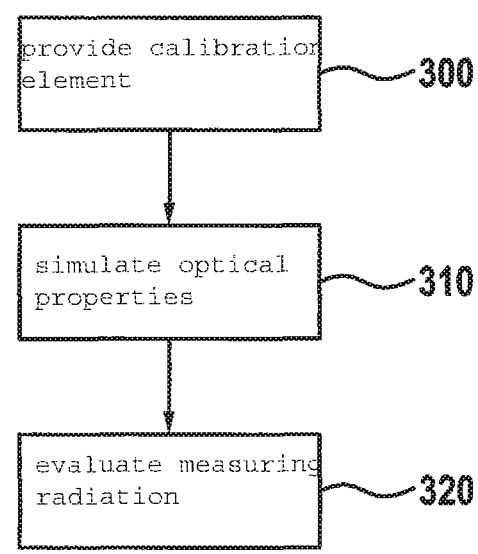
FIG. 7 shows a basic representation of a sequence of a specific embodiment of a method for calibrating an optical fluid sensor.

FIG. 7 shows a basic flow chart of a specific embodiment of a method for calibrating an optical fluid sensor 100.

In a step 300, a calibration element 50 is provided which has defined properties similar to those of a fluid 21 to be measured.

In a step 310, a simulation of optical properties of fluid 21 to be measured is carried out with the aid of calibration element 50, a measuring radiation S being routed onto calibration element 50 in the process.

Finally, in a step 320, an evaluation of measuring radiation S, modified by the calibration element, takes place, at least two calibration points of fluid 21 being ascertained in the process with the aid of calibration element 50.

Although the present invention has been described on the basis of specific application examples in the preceding text, one skilled in the art will also be able to realize specific embodiments that have not been described above or that have been described only partially, without departing from the core of the present invention.

What is claimed is:

1. A method for calibrating an optical fluid sensor, comprising:
   providing a calibration element having defined properties similar to those of a fluid to be measured;
   simulating optical properties of the fluid to be measured with the aid of the calibration element, wherein the simulating includes inserting the calibration element into a chamber at a plurality of depths and routing a measuring radiation onto the calibration element at each of the plurality of depths, thereby obtaining a plurality of radiation readings; and
   evaluating the radiation readings to produce at least one calibration point of the fluid.

2. The method as recited in claim 1, wherein the optical properties of the fluid are simulated by a defined thickness of the calibration element.

3. The method as recited in claim 1, wherein the optical properties of the fluid are simulated by a coating of the calibration element.

4. The method as recited in claim 1, wherein the optical properties of the fluid are simulated by effects at a boundary surface of the calibration element.

5. The method as recited in claim 1, wherein the calibration element is placed on boundary surfaces of an ATR crystal.

6. The method as recited in claim 1, wherein the calibration element is a Si wafer.

7. The method as recited in claim 1, wherein the calibration element is a gel.

8. A device, comprising:
   an optical fluid sensor including a chamber;
   a calibration element that is insertable into the chamber at a plurality of depths, optical properties of a fluid being simulatable with the aid of the calibration element during a calibration process in which the calibration element is inserted into the chamber at the plurality of depths to thereby obtain a plurality of radiation measurements that respectively correspond to the plurality of depths; and
   processing circuitry, wherein the processing circuitry is arranged such that the plurality of radiation measurements are receivable by the processing circuitry, the plurality of radiation measurements being evaluable by the processing circuitry to produce a plurality of calibration points.

9. The device as recited in claim 8, wherein a transmissivity of radiation through the calibration element varies along a length of the calibration element.

10. The device as recited in claim 9, wherein the chamber is a fluid channel into which the calibration element is able to be introduced during the calibration process and from which the calibration element is able to be removed following the calibration process.

11. The device as recited in claim 9, wherein a reflection behavior of the fluid is able to be simulated with the aid of a reflection layer applied on the calibration element.

12. The device as recited in claim 9, wherein a transmittance behavior of the fluid is able to be simulated with the aid of a thickness of the calibration element.

13. A device comprising:
   a fluid channel that include fluid openings distal from a proximal end of the fluid channel;
   a radiation source arranged at a first side of the proximal end of the fluid channel opposite the fluid openings;
   an optical detector also arranged at the first side of the proximal end of the fluid channel opposite the fluid openings;
   a solid or gel calibration element that is removably located within the fluid channel between the fluid openings and the proximal end of the fluid channel, wherein:
      optical properties of a fluid are simulatable with the calibration element during a calibration process in which radiation is emitted by the radiation source and reflected back to the optical detector through the calibration element to obtain a radiation measurement; and
      the radiation source, fluid channel, calibration element, and optical detector are arranged relative to each other such that, during the calibration process, the emitted radiation, bypassing the calibration element, is able to reach a reflective portion of the fluid channel that is more distal from the proximal end of the fluid channel than is the calibration element and by which the emitted radiation is reflected towards and through the calibration element, onwards to the optical detector; and
   processing circuitry communicatively coupled to the optical detector, the radiation measurement thereby being deliverable to the processing circuitry so that a calibration point is recordable by the processing circuitry based on the radiation measurement.

14. A device comprising:
   a removable calibration element;
   a radiation source;
   an optical detector, wherein:
      the radiation source and the optical detector are at a same side of the calibration element;
      the calibration element is a solid or a gel; and
      optical properties of a fluid are simulatable with the calibration element during the calibration process in which radiation is emitted by the radiation source and reflected back to the optical detector by or through the calibration element to obtain a radiation measurement;
   processing circuitry communicatively coupled to the optical detector, the radiation measurement thereby being deliverable to the processing circuitry so that a calibration point is recordable by the processing circuitry based on the radiation measurement; and
   an attenuated total reflectance (ATR) crystal arranged between (a) the calibration element removably applied to a first side of the ATR crystal and (b) both the radiation source and optical detector at a second side of the ATR crystal, the second side being opposite the first side.

15. The device as recited in claim 14, wherein the calibration element is reflective and is arranged relative to the radiation source so that radiation emitted by the radiation source towards the calibration is reflected by the calibration element to the optical detector.

* * * * *